United States Patent
da Silva (10) Patent No.: US 12,268,811 B2
(45) Date of Patent: Apr. 8, 2025

(54) ESTIMATION OF CARDIOGENIC ARTEFACTS ON VENTILATOR AIRWAY PRESSURE AND FLOW FOR THE AUTOMATED DETECTION AND RESOLUTION OF PATIENT VENTILATOR ASYNCHRONIES

(71) Applicant: KONINKLIJKE PHILIPS N.V., Eindhoven (NL)

(72) Inventor: Ikaro Garcia Araujo da Silva, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 746 days.

(21) Appl. No.: 17/403,913

(22) Filed: Aug. 17, 2021

(65) Prior Publication Data

US 2022/0072246 A1 Mar. 10, 2022

Related U.S. Application Data

(60) Provisional application No. 63/074,550, filed on Sep. 4, 2020.

(51) Int. Cl.
*A61M 16/00* (2006.01)
*G06N 20/00* (2019.01)

(52) U.S. Cl.
CPC .... *A61M 16/0051* (2013.01); *A61M 16/0003* (2014.02); *A61M 16/026* (2017.08);
(Continued)

(58) Field of Classification Search
CPC ............ A61M 16/026; A61M 16/0003; A61M 16/069; A61M 2203/05; A61M 2016/003;
(Continued)

(56) References Cited

U.S. PATENT DOCUMENTS

2006/0107953 A1* 5/2006 Truschel ............. A61M 16/024
128/204.23
2008/0110461 A1* 5/2008 Mulqueeny ....... A61M 16/0051
128/204.23

(Continued)

OTHER PUBLICATIONS

Imanaka et al. "Autotriggering caused by cardiogenic oscillation during flow-triggered mechanical ventilation". Crit. Care Med. 2000; 28(2); 402-407 (Year: 2000).*

(Continued)

*Primary Examiner* — Timothy A Stanis
*Assistant Examiner* — Sara K Toich
(74) *Attorney, Agent, or Firm* — Daniel H. Brean; Andrew M. Gabriel (57) ABSTRACT

A method of identifying the occurrence of patient-ventilator asynchrony (PVA) includes using a cardiogenic index generated from a number of breath attribute signals measured by ventilators. The method can be implemented in a ventilator by a controller that includes a machine learning model trained to use the cardiogenic index and other features extracted from ventilator waveforms to identify the occurrence of PVAs. A ventilator equipped with such a controller can provide real-time alerts to a caregiver that a PVA has occurred so that the ventilator settings can be adjusted.

20 Claims, 7 Drawing Sheets

(52) U.S. Cl.
CPC ......... *G06N 20/00* (2019.01); *A61M 2230/04* (2013.01); *A61M 2230/40* (2013.01)

(58) Field of Classification Search
CPC ...... A61M 2016/0036; A61M 2230/40; A61M 2230/04; A61B 5/0205; A61B 5/087; A61B 5/091; A61B 5/7264; A61B 5/7278; A61B 5/02416; A61B 2560/0223; A61B 2560/0238; G06N 20/00
See application file for complete search history.

(56) References Cited

U.S. PATENT DOCUMENTS

| | | | |
|---|---|---|---|
| 2013/0025597 A1* | 1/2013 | Doyle | A61B 5/14551 128/204.23 |
| 2015/0289785 A1 | 10/2015 | Bojovic | |
| 2016/0279361 A1* | 9/2016 | Mulqueeny | A61B 5/085 |
| 2019/0320973 A1* | 10/2019 | Martin | A61B 5/4812 |
| 2020/0054520 A1 | 2/2020 | Adams | |
| 2021/0205558 A1 | 7/2021 | Albanese | |
| 2021/0220587 A1 | 7/2021 | Gholami | |
| 2022/0020488 A1* | 1/2022 | Kennedy | G16H 50/20 |

OTHER PUBLICATIONS

Blanch, L., Sales, B., Montanya, J. et al. "Validation of the Better Care® system to detect ineffective efforts during expiration in mechanically ventilated patients: a pilot study". Intensive Care Med 38, 772-780 (2012) (Year: 2012).*
Holanda MA, Vasconcelos RDS, Ferreira JC, Pinheiro BV. Patient-ventilator asynchrony. J Bras Pneumol. Jul.-Aug. 2018 44(4):321-333. doi: 10.1590/S1806-37562017000000185. Epub Jul. 6, 2018. Erratum in: J Bras Pneumol. Sep. 3, 2018 (Year: 2018).*
Sinderby C, Liu S, Colombo D, Camarotta G, Slutsky AS, Navalesi P, Beck J. An automated and standardized neural index to quantify patient-ventilator interaction. Crit Care. Oct. 16, 2013;17(5):R239 (Year: 2013).*
Glauco M Plens, Caio CA Morais, Maria A Nakamura, Patricia N Souza, Marcelo BP Amato, Mauro R Tucci and Eduardo LV Costa. Effect of Cardiogenic Oscillations on Trigger Delay During Pressure Support Ventilation. Respiratory Care Jul. 2018, 63 (7) 865-872 (Year: 2018).*
International Search Report for PCT/EP2021/073236 filed Aug. 23, 2021.
Ramirez, I.I. et al., "Identifying Patient-Ventilator Asynchrony Using Waveform Analysis", Palliative Medicine & Care: Open Access, vol. 4, No. 4 (Dec. 4, 2017), pp. 1-4.
Arbour, R. "Cardiogenic Oscillation and Ventilator Autotriggering in Brain-Dead Patients: A Case Series". American Journal of Critical Care, Sep. 2009, vol. 18, No. 5.

* cited by examiner

ESTIMATION OF CARDIOGENIC ARTEFACTS ON VENTILATOR AIRWAY PRESSURE AND FLOW FOR THE AUTOMATED DETECTION AND RESOLUTION OF PATIENT VENTILATOR ASYNCHRONIES

CROSS-REFERENCE TO RELATED APPLICATIONS

This patent application claims the priority benefit under 35 U.S.C. § 119(e) of U.S. Provisional Application No. 63/074,550, filed on Sep. 4, 2020, the contents of which are herein incorporated by reference.

BACKGROUND OF THE INVENTION

1. Field of the Invention

The disclosed concept pertains to methods for detecting patient-ventilator asynchrony (PVA), and, in particular, to a method for detecting non-airway factors indicative of PVAs in order to identify and resolve PVAs.

2. Description of the Related Art

Around 800,000 patients receive ventilation therapy support in Intensive Care Units (ICUs) across the United States every year. Mechanical ventilation is typically instituted when a patient is unable to maintain adequate ventilation or oxygenation, and hence gas exchange, on their own. While mechanical ventilators are designed to provide life-critical support to the patient, learning how to operate and tune the ventilator settings to complex patient conditions can be a daunting task to even the most experienced Intensivists and Respiratory Therapists. A key component for identifying optimal settings on mechanical ventilators is the avoidance of patient-ventilator asynchrony (PVA). PVAs occur when the ventilator and the patient operate out of phase, or in conflict, with each other. PVAs are estimated to be present in as much as 88% of mechanically ventilated patients. The occurrence of PVAs has the potential to affect the outcome and quality of life of mechanically ventilated patients. Some of the potential risks associated with PVAs that have been reported in the scientific literature are a 3-fold increase in duration of ventilation, an 8-fold increase in tracheostomy rate, and a 2-fold increase in ICU length of stay, among others.

Given the significant increase in risk outcomes that can result from PVAs, swift detection of PVAs is important. However, the current primary method for detecting PVAs consists of caregivers manually analyzing ventilator waveforms, which does not lend itself to real-time detection of PVAs. Accordingly, there is room for improvement in methods and systems for detecting PVAs.

SUMMARY OF THE INVENTION

Accordingly, it is an object of the present invention to provide, in one embodiment, a method of identifying the occurrence of a patient-ventilator asynchrony (PVA) by measuring a number of breath attribute signals of a patient receiving respiration assistance from a ventilator, generating a cardiogenic index from the number of breath attribute signals, and analyzing the cardiogenic index to determine whether a PVA has occurred.

In another embodiment, a ventilator comprises: a controller, an inflow pathway structured to provide air from the ventilator into an airway of a patient, an outflow pathway structured to receive expired air from the airway of the patient, and a number of sensors structured to measure data about the patient breath attributes, wherein the controller is structured to receive data measured by the number of sensors and to generate a cardiogenic index based on the data measured by the sensors, and to analyze the cardiogenic index to determine whether a PVA has occurred.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise.

As used herein, the statement that two or more parts or components are "coupled" shall mean that the parts are joined or operate together either directly or indirectly, i.e., through one or more intermediate parts or components, so long as a link occurs.

As used herein, the term "number" shall mean one or an integer greater than one (i.e., a plurality).

As used herein, the term "controller" shall mean a number of programmable analog and/or digital devices (including an associated memory part or portion) that can store, retrieve, execute and process data (e.g., software routines and/or information used by such routines), including, without limitation, a field programmable gate array (FPGA), a complex programmable logic device (CPLD), a programmable system on a chip (PSOC), an application specific integrated circuit (ASIC), a microprocessor, a microcontroller, a programmable logic controller, or any other suitable processing device or apparatus. The memory portion can be any one or more of a variety of types of internal and/or external storage media such as, without limitation, RAM, ROM, EPROM(s), EEPROM(s), FLASH, and the like that provide a storage register, i.e., a non-transitory machine readable medium, for data and program code storage such as in the fashion of an internal storage area of a computer, and can be volatile memory or nonvolatile memory.

As used herein, the term "machine learning model" shall mean a software system that develops and builds a mathematical model based on sample data, known as "training data", in order to make predictions or decisions without being explicitly programmed to do so, including, without limitation, a computer software system that develops that has been trained to recognize patterns from a set of training data, and subsequently develops algorithms to recognize patterns from the training data set in other data sets.

As used herein, the term "cardiogenic artefact" shall mean distortions on airway pressure and flow waveforms due to mechanical activity from the heart and its pulsatile blood flow.

As used herein, the term "cardiogenic index" shall mean a measure, e.g., a signal, that is indicative of the amount of cardiogenic artefacts that are present on both the pressure and flow waveforms of a ventilator over a period of time and/or collection of samples.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept, as described in greater detail herein in connection with various particular exemplary embodiments, provides methods and systems for the automated detection and resolution of PVAs for a patient receiving mechanical ventilation. Depending on the needs of a particular patient, a ventilator may be set to either an assist mode or a mandatory mode. In an assist mode, the ventilator is set to provide a breath to the patient's airway upon detection of a perceived inhalation effort from the patient. One way to detect inhalation effort is to establish the patient's baseline esophageal pressure and monitor the patient's ongoing esophageal pressure so that any increases from the baseline esophageal pressure can be categorized as inhalation efforts. In a mandatory mode, the ventilator is set to provide breaths at predetermined regular intervals.

The disclosed concept addresses the detection and resolution of two specific types of PVAs that can occur when a ventilator is set to an assist mode: auto triggering and ineffective triggering. Auto triggering occurs when the patient has not made an effort to inhale and the ventilator delivers a breath regardless. Ineffective triggering occurs when the patient does make an effort to inhale and the ventilator fails to deliver a breath.

Figure 1:
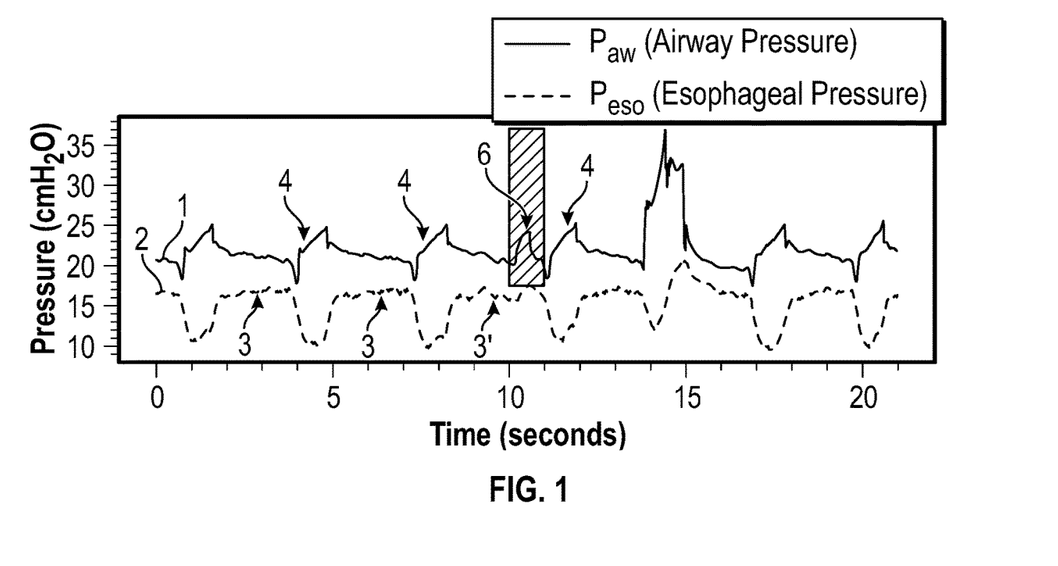
FIG. 1 shows a graph of a waveform to illustrate the occurrence of an auto triggering PVA.

FIG. 1 is a graph showing a patient's airway pressure waveform 1 with the patient's concurrent esophageal pressure waveform 2 so as to demonstrate the occurrence of an auto triggering PVA. The plateau regions 3 in esophageal pressure waveform 2 denote the patient's inhalation efforts. Airway pressure waveform 1 depicts the patient's time-varying airway pressure resulting from the ventilator supplying breaths to the patient. When the ventilator operates in the intended manner, an increasing slope 4 in ventilator waveform 1 should coincide with the conclusion of a plateau region 3, indicating that the ventilator is supplying a breath to the patient as a result of detecting the conclusion of the patient's inhalation effort. Highlighted around the 10-second mark of the x-axis is an auto triggering PVA peak 6 in ventilator waveform 1. Peak 6 is classified as an auto triggering PVA because the ventilator supplied the breath to the patient when the patient was still in the midst of an inhalation effort rather than at the conclusion of the patient's inhalation effort. Plateau region 3' has more pronounced variation in pressure than other plateau regions 3, which is ostensibly the cause of the auto triggering PVA, indicating that the auto triggering PVA may have arisen due to hypersensitive ventilator settings.

Figure 2:
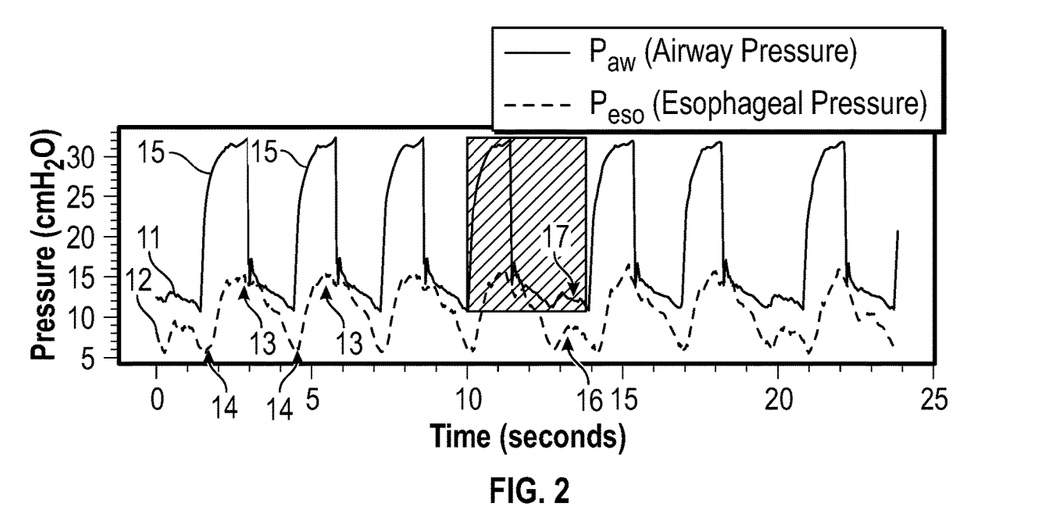
FIG. 2 shows a graph of a waveform to illustrate the occurrence of an ineffective triggering PVA.

FIG. 2 is a graph showing a patient's airway pressure waveform 11 with the patient's concurrent esophageal pressure waveform 12 so as to demonstrate the occurrence of an ineffective triggering PVA. The domed regions 13 of esophageal pressure waveform 12, with their demonstrated increases from the patient's baseline esophageal pressure 14, denote the patient's inhalation efforts. Airway pressure waveform 11 depicts the patient's time-varying airway pressure resulting from the ventilator supplying breaths to the patient. When the ventilator operates in the intended manner, the start of an initial increasing slope of a sharkfin wave 15 in ventilator waveform 11 coincides with the start of an initial increasing slope of a domed region 13, indicating that the ventilator is supplying a breath to the patient as a result of detecting the patient's commencement of an inhalation effort. Highlighted around the 13-second mark of the x-axis, there is an ineffective triggering PVA interval 17 in airway pressure waveform 11 that coincides with a domed region 16. Interval 17 is classified as an ineffective PVA because, although the domed region 16 exhibits an increase from the patient's baseline esophageal pressure 14 around the 13-second mark to denote the start of an inhalation effort, there is no significant increase in the airway pressure waveform 11 at interval 17, signifying that the ventilator failed to deliver a recommended breath to the patient. Domed region 16 has a noticeably smaller amplitude than other domed regions 13, which is ostensibly the cause of the ineffective triggering PVA, indicating that the PVA may have arisen due to hyposensitive ventilator settings.

Figure 3:
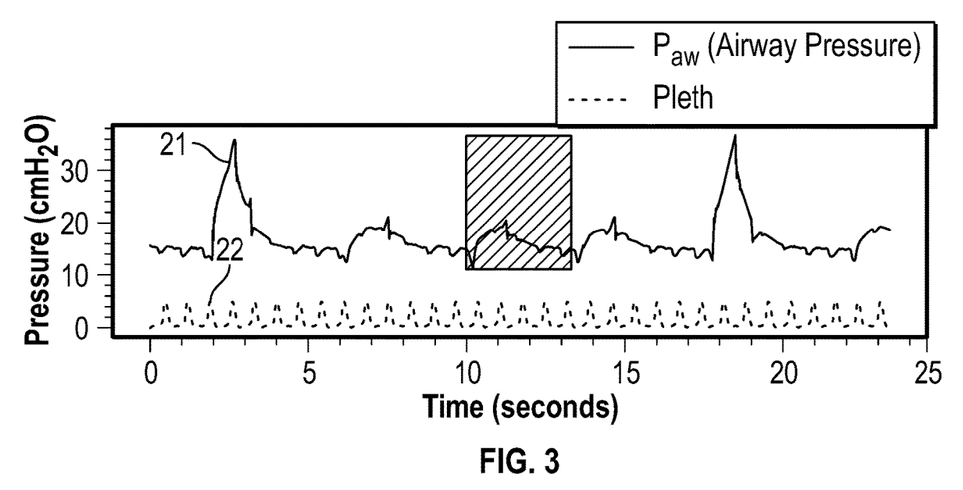
FIG. 3 shows a graph that includes both a ventilator airway pressure waveform and a photoplethysmogram (PPG) signal to illustrate an association between airway pressure waveforms and PPG signals.

Anecdotal evidence suggests that: (1) cardiogenic oscillations present in ventilator airway pressure waveforms often trigger delivery of breath by a ventilator and are responsible for a large proportion of auto triggering asynchronies, and (2) the presence of significant cardiogenic components in ventilator airway pressure waveform data often yields false detection of ineffective triggering or makes identification of ineffective triggering extremely difficult. FIG. 3 is a graph displaying a ventilator waveform 21 with a concurrent photoplethysmogram (PPG) signal 22 produced by a pulse oximeter so as to illustrate an association between cardiogenic signals (in the format of PPG signals) and ventilator airway pressure signals. It will be appreciated that PPG signals are not available on ventilators, hence why PPG signal 22 is provided by a pulse oximeter. Ventilator waveform 21 depicts a patient's time-varying airway pressure resulting from a ventilator supplying breaths to the patient. The concurrent display of PPG signal 22 with ventilator waveform 21 highlights the synchronization of significant decreases in ventilator waveform 21 with peaks in PPG signal 22, suggesting an association between cardiogenic artefacts and changes in ventilator-based airway pressure.

Engineers typically regard cardiogenic artefacts as noise and attempt to remove it prior to any processing of airway pressure waveforms. The present disclosure posits that a significant number of asynchrony events appear because of the presence of cardiogenic artefacts, and thus, cardiogenic artefacts should be treated as a signal of interest rather than noise. In addition, the process of removing cardiogenic artefacts from ventilator waveforms is difficult because: (1) there is significant overlap between ventilator signals of interest and cardiogenic signal, and (2) conditions in the human body related to ventilator signals and cardiogenic interactions are highly non-stationary, so any strategy to detect the overlap between the ventilator signals of interest and cardiogenic signals would require frequent updating. It is therefore an objective of the present disclosure to present an algorithm to calculate the cardiogenic component present in ventilator waveforms as a discrete component of those waveforms and quantify it in a cardiogenic index such that the cardiogenic index can be used to detect and resolve PVAs. Calculating cardiogenic artefacts as a discrete component of ventilator waveforms represents an improvement over prior art systems and methods for identifying PVAs.

Figure 4:
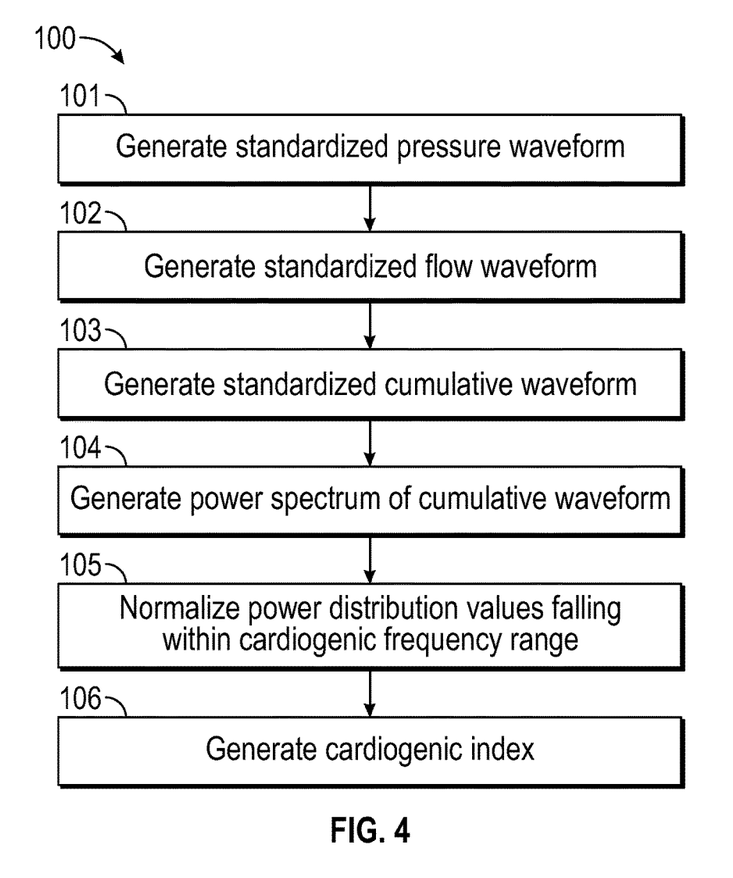
FIG. 4 is a flow chart containing the steps of a method for calculating a cardiogenic index from ventilator waveforms according to an exemplary embodiment of the disclosed concept.
Figure 5A:
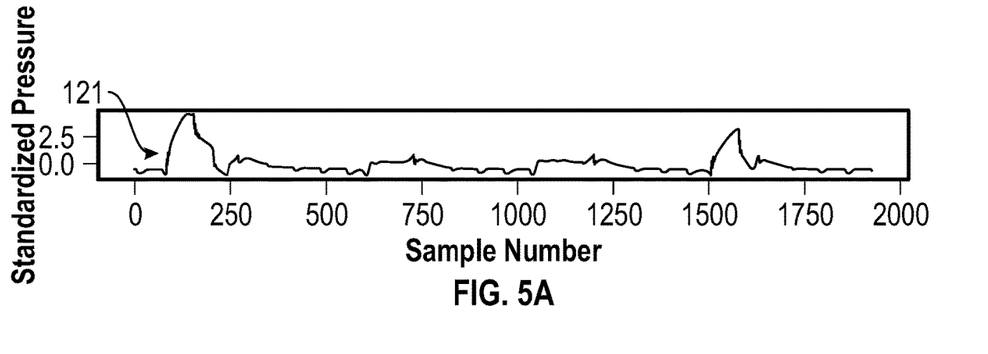
FIGS. 5A-5D show graphs of waveforms corresponding to the steps of the method shown in the flow chart of FIG. 4.

FIG. 4 is a flow chart of a method 100 for calculating a cardiogenic index from the cardiogenic artefacts present in ventilator airway pressure and flow waveforms. Waveforms corresponding to the steps of the method 100 are shown in FIGS. 5A-5D. At 101, the data points comprising the pressure waveform of a ventilator are standardized using Equation (1) below:

$$z_{Py(t_i)} = \frac{Py(t_i) - \bar{\mu}_{Py(t)}}{\sigma_{Py(t)}} \quad (1)$$

where t is time, n is the total number of data points in the pressure waveform such that $1 \leq i \leq n$, $Py(t_i)$ is the value of the $i^{th}$ data point of the ventilator pressure waveform, $\bar{\mu}_{Py(t)}$ is the mean of the n pressure waveform y-values, $\sigma_{Py(t)}$ is the standard deviation of the n pressure waveform y-values, and $z_{Py(t_i)}$ is the standardized value of $Py(t_i)$. In addition, $z_{Py(t)}$ represents the standardized pressure waveform function. In typical ventilator pressure waveforms, the x-axis units are seconds and the y-axis units are $cmH_2O$. In the standardized pressure waveform, the x-axis units are sample number instead of seconds and the y-axis is unitless. Referring to FIG. 5A, a graph of an example standardized pressure waveform 121 is shown.

Figure 5B:
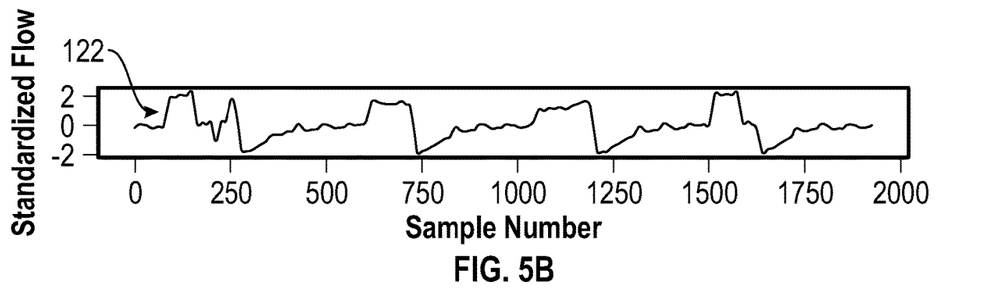

At 102, the data points comprising the flow waveform of a ventilator are standardized using Equation (2) below:

$$z_{Q(t_i)} = \frac{Q(t_i) - \bar{\mu}_{Q(t)}}{\sigma_{Q(t)}} \quad (2)$$

where t is time, n is the total number of data points in the pressure waveform such that $1 \leq i \leq n$, $Q(t_i)$ is the value of the $i^{th}$ data point of the ventilator flow waveform, $\bar{\mu}_{Q(t)}$ is the mean of the n flow waveform y-values, $\sigma_{Q(t)}$ is the standard deviation of the n flow waveform y-values, and $z_{Q(t_i)}$ is the standardized value of $Qy(t_i)$. In addition, $z_{Q(t)}$ represents the standardized flow waveform function. In typical ventilator flow waveforms, the x-axis units are seconds and the y-axis units are L/min. In the standardized flow waveform, the units of the x-axis are sample number instead of seconds and the y-axis is unitless. Referring to FIG. 5B, a graph of an example standardized flow waveform 122 is shown.

Standardized pressure waveform 121 and standardized flow waveform 122 represent concurrent patient airway data such that a data point with x-coordinate $x_i$ on standardized pressure waveform 121 is from the same sample number (or same point in time, with respect to the original ventilator waveform) as a data point with x-coordinate $x_i$ on standardized flow waveform 122 and vice versa. It will be appreciated that the data points comprising the flow waveform of a ventilator could be standardized at 101 instead of 102 and that the data points comprising the pressure waveform of a ventilator could instead be standardized at 102 instead of 101 without departing from the disclosed concept.

At 103, the standardized waveforms $z_{Py(t)}$ and $z_{Q(t)}$ are summed to create a standardized cumulative waveform z(t). As with the standardized waveforms $z_{Py(t)}$ and $z_{Q(t)}$, the units of standardized cumulative waveform x-axis are sample number and the y-axis is unitless. The summation of $z_{Py(t)}$ and $z_Q(t)$ emphasizes the physiological signals that are synchronized across the pressure and flow waveforms, the assumption being that the cardiogenic signal is synchronized across the pressure and flow waveforms and other noise sources are not. Thus, cumulative waveform z(t) should yield a stronger cardiogenic component than either the pressure waveform $z_{Py(t)}$ or flow waveform $z_{Q(t)}$ taken alone would.

Figure 5C:
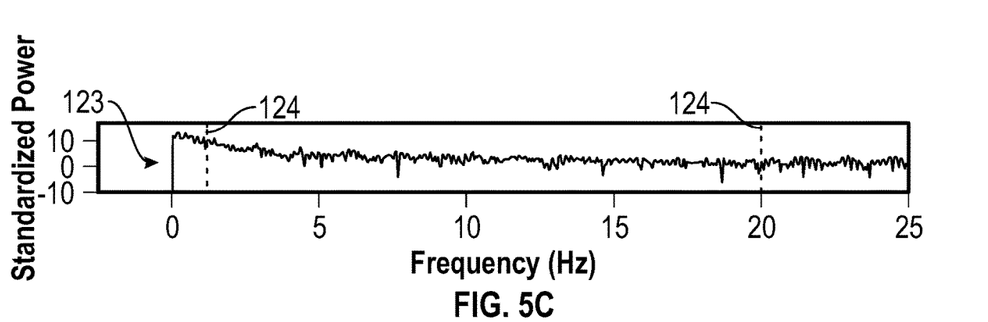

At 104, a power spectrum P(f) of cumulative waveform z(t) is calculated by taking the fast Fourier transform of z(t), with frequency being measured in Hertz. Referring to FIG. 5C, an example power spectrum 123 of a standardized cumulative waveform is shown, the standardized cumulative waveform having been generated by summing standardized pressure waveform 121 and standardized flow waveform 122. Empirical results from a retrospective clinical datasets where ventilator pressure and flow settings were fine-tuned based upon concurrent PPG signals suggest that cardiogenic signal power is the most prevalent component of cumulative ventilator pressure-flow waveforms in the 1.2 Hz to 20 Hz frequency range. The 1.2 Hz to 20 Hz frequency region is denoted by lines 124 in FIG. 5C. Datasets compiled from a greater number of patients and/or using different models of ventilators may show cardiogenic signals prevailing in frequency regions other than the 1.2 Hz to 20 Hz region. It will be appreciated that, if cardiogenic signals are indeed found to prevail in a frequency region other than the 1.2 Hz to 20 Hz region for a given set of conditions, the lower frequency boundary and upper frequency boundary of the frequency region in which cardiogenic signals actually prevail should be substituted for the 1.2 Hz and 20 Hz frequency boundaries, respectively, in steps 105 and 106 (described in further detail herein), and that doing so is within the scope of the disclosed concept.

At 105, the standardized power distribution values in the 1.2 Hz to 20 Hz frequency region of P(f) are normalized in order to bound those distribution values between 0 and 1 using Equation (3) below:

$$P(f_i)_{norm} = \frac{P(f_i)}{\sum_{f=0}^{F_s/2} P(f)}, \text{ for } 1.2 \leq f_i \leq 20 \tag{3}$$

where f is measured in Hertz, $P(f_i)$ is the distribution value of frequency $f_i$ in P(f), $F_s/2$ is the upper bound of the first Nyquist zone of P(f), and $P(f_i)_{norm}$ is the normalized value of $P(f_i)$ bounded between 0 and 1. The expression $$\sum_{f=0}^{F_s/2} P(f)$$

functionally equates to the sum of all power present in P(f), i.e., both cardiogenic signal power and all non-cardiogenic signal power. In practice, $F_s/2$ is the upper bound of the cardiogenic frequency range, i.e., 20 Hz, signifying that the 0 Hz to 1.2 Hz frequency region of power spectrum P(f) is comprised primarily of the components of the ventilator waveforms not influenced by a cardiogenic signal. It will be appreciated that a frequency somewhat lower or higher than 1.2 Hz may be used as the delineator between the frequency region that is comprised primarily of cardiogenic signal components and the frequency region that is comprised primarily of non-cardiogenic signal components without departing from the scope of the disclosed concept. It will also be appreciated that the upper bound of the cardiogenic frequency range and $F_s/2$ may be somewhat lower or higher than 20 Hz without departing from the scope of the disclosed concept. It will be further appreciated that cardiogenic signal power can alternatively be estimated using techniques such as harmonic spectral analysis (based on external or derived heart rate measurements) or auto-regressive modelling without departing from the scope of the disclosed concept.

Figure 5D:
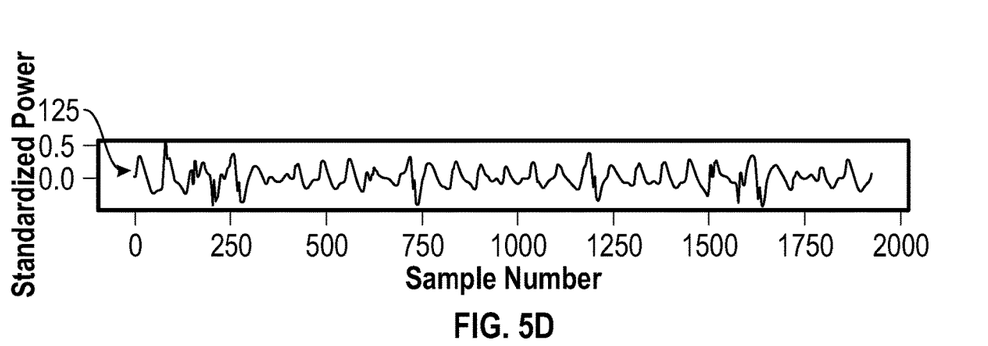

At 106, a cardiogenic index in the form of a standardized cardiogenic signal is reconstructed by performing the inverse fast Fourier transform on only the normalized distribution values in the 1.2 Hz to 20 Hz region of P(f) calculated at 105. Referring to FIG. 5D, a graph of an example standardized cardiogenic signal 125 reconstructed from the normalized distribution values in the 1.2 Hz to 20 Hz region of power spectrum 123 is shown and plotted on a same scale x-axis as the standardized pressure and flow waveforms 121, 122. It will be appreciated that normalizing the distribution values in the 1.2 Hz to 20 Hz region of P(f) at 105 facilitates the use of the standardized cardiogenic signal as a cardiogenic index, as the values of the standardized cardiogenic signal will always be bounded between 0 and an absolute value of 1. Standardized cardiogenic signal 125 shows the extracted cardiogenic components of the combined standardized pressure and flow waveforms 121, 122 such that a data point with x-coordinate $x_i$ on the standardized cardiogenic signal waveform 125 corresponds to the same point in time or the same sample number as the data point with x-coordinate $x_i$ on standardized pressure waveform 121 and the data point with x-coordinate $x_i$ on standardized pressure waveform 122 and vice versa.

Figure 6:
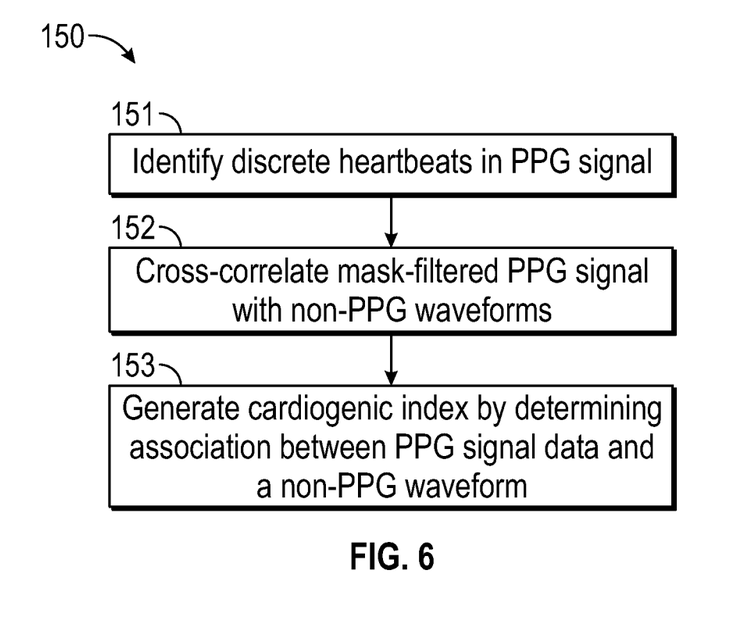
FIG. 6 is a flow chart containing the steps of a method for calculating a cardiogenic index from a ventilator PPG waveform according to an exemplary embodiment of the disclosed concept.
Figure 7A:
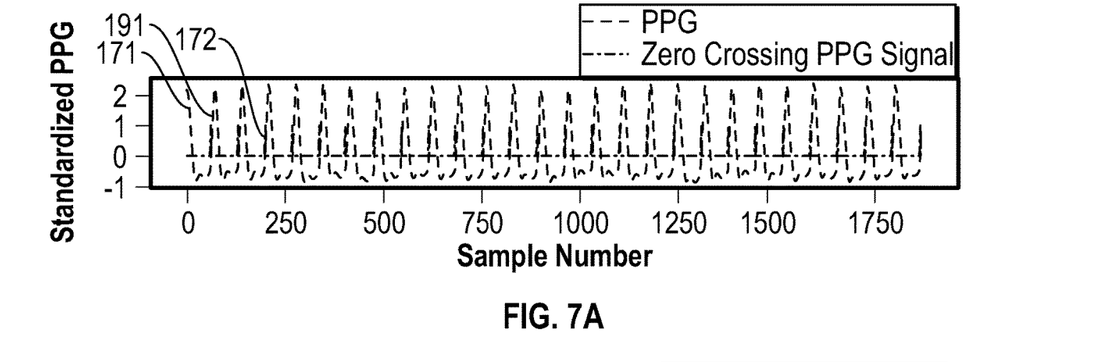
FIGS. 7A-7C show graphs of waveforms corresponding to the steps of the method shown in the flow chart of FIG. 6.
Figure 7B:
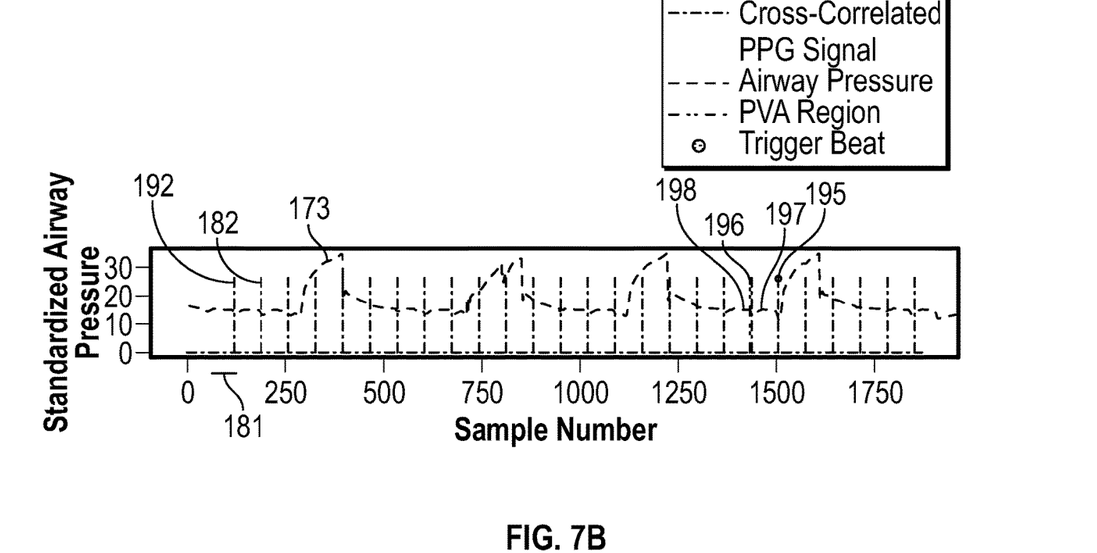
Figure 7C:
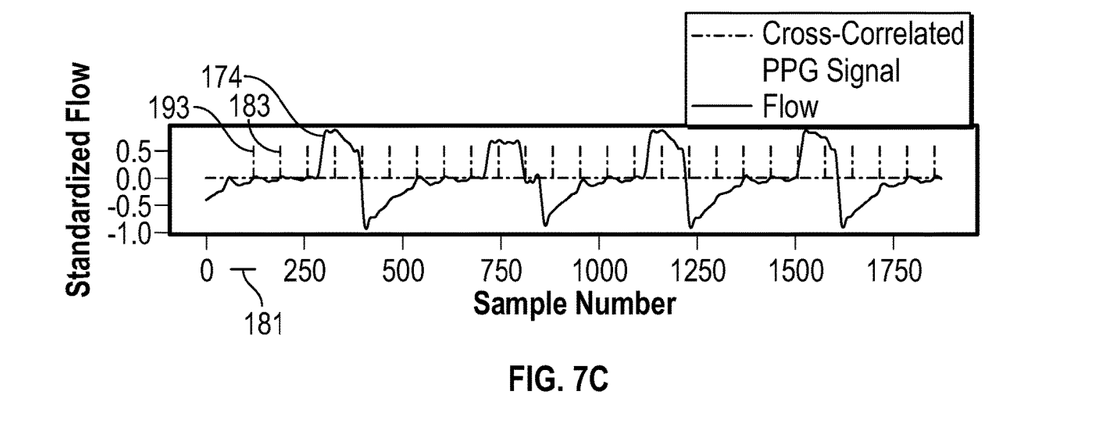

To the extent that ventilators with the capability to generate PPG signals are available or become available, cardiogenic signal power may be estimated from the ventilator-provided PPG signal directly (i.e., without performing steps 101 through 105 of method 100 to extract the cardiogenic signal data from ventilator airway pressure and flow waveforms) without departing from the scope of the disclosed concept. Referring to FIG. 6, in an additional non-limiting exemplary embodiment of the disclosed concept, provided that a ventilator is capable of generating a PPG signal, a cardiogenic index can be calculated using a method 150 instead of method 100. FIG. 6 is a flow chart of method 150 and FIGS. 7A-7C show graphs of waveforms associated with the steps of method 150.

At 151, discrete heartbeats in the PPG signal are identified using zero crossing, thresholding, or any other technique suitable for detecting discrete data in a continuous signal. Such techniques often employ the use of a signal mask, e.g. a zero crossing mask. Step 151 is subsequently discussed in terms of applying a mask for purposes of brevity, however, it will be appreciated that use of the term "mask" is intended to be non-limiting and does not exclude the use of techniques for detecting discrete heartbeats in the PPG signal that do not employ a signal mask. FIG. 7A is a graph of a theoretical ventilator-provided PPG signal 171 and a zero crossing PPG signal 172 that results from filtering PPG signal 171 with a zero crossing mask. Each peak in zero crossing PPG signal 172 identifies the onset of a discrete heartbeat in PPG signal 171.

At 152, after discrete heartbeats have been identified in the PPG signal by applying a signal mask (or using another suitable technique), the mask-filtered PPG signal is cross-correlated with the other non-PPG ventilator waveforms, for example and without limitation, airway pressure and flow waveforms. Cross-correlating the mask-filtered PPG signal with the exhalation phase of the non-PPG ventilator waveforms in particular is preferable, as the exhalation phase is less corrupted by ventilator mechanics than the inhalation phase. FIGS. 7B and 7C show graphs of cross-correlated PPG signals 182, 183 that result from cross-correlating zero crossing PPG signal 172 with the exhalation phase of standardized airway pressure and flow waveforms 173, 174 and lag zero crossing PPG signal 172 by a time shift 181. Time shift 181 can be understood by observing first peaks 192, 193 of cross-correlated PPG signals 182, 183 in relation to a first peak 191 of zero crossing PPG signal 172. First peaks 192, 193 are offset from first peak 191 by time shift 181, and it will be appreciated that every subsequent $n^{th}$ peak of cross-correlated PPG signals 182, 183 is offset from the corresponding $n^{th}$ peak of zero crossing PPG signal 172 by time shift 181 as well. As with the peaks of zero crossing PPG signal 172, the peaks of cross-correlated PPG signals 182, 183 (such as first peaks 192, 193) denote the onset of individual heartbeats.

At 153, a cardiogenic index is generated by determining an association between the cardiogenic data in the PPG signal and at least one of the other non-PPG ventilator waveforms (i.e., the airway pressure or flow waveform). In a first non-limiting example, breath delivery regions and non-breath delivery regions of a non-PPG waveform are identified, and signal to noise ratios (SNRs) generated by comparing values from the breath delivery regions to values from nearby non-breath delivery regions can be used as the cardiogenic index. First, breath delivery intervals in the non-PPG waveform that correspond to time intervals when the ventilator is delivering a breath to the patient are identified. The heartbeat immediately preceding each breath delivery interval is deemed a heartbeat of interest, and the interval of the non-PPG waveform corresponding to the heartbeat of interest is deemed an interval of interest. Because the onset of each heartbeat in cross-correlated PPG signals such as cross-correlated PPG signals 182, 183 is represented by a peak that spans a theoretically infinitesimally small interval of time, when reference is made to an interval of interest in the non-PPG signal, it will be appreciated that a determination must be made about what length of time the interval of interest spans. An interval of 50 milliseconds is suggested as being of sufficient duration for the purpose of yielding enough data to generate a meaningful cardiogenic index, but it will be appreciated that longer or shorter intervals of time may be used without departing from the scope of the disclosed concept. Referring to FIG. 7B and using airway pressure waveform 173 as a non-limiting example of a non-PPG waveform that can be used to calculate the SNR, peak 195 on cross-correlated PPG signal 182 corresponds to a breath delivery interval of airway pressure waveform 173 (as determined extrinsically), and peak 196 on cross-correlated PPG signal 182 marks the onset of the heartbeat of interest relative to peak 195. Incidentally, the breath delivered during the interval associated with peak 195 is a PVA. A 50 millisecond (or other chosen duration) interval 197 of airway pressure waveform 173 that commences where airway pressure waveform 173 coincides with peak 196 is the interval of interest.

A SNR is determined by comparing: (1) the range of distortion of the non-PPG signal values in the interval of interest to (2) the values of the non-PPG signal in a region that does not coincide with a heartbeat and is in close proximity to the interval of interest. Referring again to FIG. 7B, region 198 of airway pressure waveform 173 is a region close to the interval of interest (interval 197) that does not coincide with a heartbeat. An exemplary SNR for airway pressure waveform 173 can be determined by comparing the range of distortion of the airway pressure values in interval 197 (the interval of interest) to the airway pressure values in region 198 (the region close to the interval of interest that does not coincide with a heartbeat).

The range of distortion of the non-PPG signal in an interval of interest will be significantly greater immediately before the occurrence of a PVA than before the occurrence of a correctly-provided ventilator-delivered breath. Accordingly, the SNRs calculated for PVA-associated regions of the non-PPG signal will be easily discernible from the SNRs calculated for the regions of the non-PPG signal associated with correctly-provided ventilator-delivered breaths. This discernibility is what renders the SNRs suitable for use as a cardiogenic index for the detection of PVAs.

In another non-limiting example of how the cardiogenic index can be calculated at 153, another type of SNR, distinct from the type described in the previous non-limiting example, can be determined and used as the cardiogenic index. First, the dominant frequency spectrum of the PPG signal and its harmonics are determined, for example, via spectral analysis. Then, for a chosen non-PPG signal ventilator waveform (e.g. an airway pressure waveform or a flow waveform), the SNR can be calculated for different regions of the non-PPG waveform by finding the ratio of the PPG-dominant frequency components to the non-PPG-dominant frequency components present in each region of the waveform. The ratio of the PPG-dominant frequency components to the other frequency components will be significantly greater prior to the occurrence of a PVA than prior to the occurrence of a correctly-provided ventilator-delivered breath. The SNRs calculated for PVA-associated regions of the non-PPG waveform will be easily discernible from the SNRs calculated for the regions of the non-PPG waveform associated with correctly-provided ventilator-delivered breaths, and this discernibility is what renders the SNRs suitable for use as a cardiogenic index for the detection of PVAs.

Method 100 is referenced throughout the present disclosure as a means for calculating a cardiogenic index, for example with respect to the descriptions of methods 200 and 300, and it will be appreciated that, for any ventilator capable of providing a PPG, method 150 may be employed instead of method 100 without departing from the scope of the disclosed concept. In addition, the PPG analysis described with respect to method 150 can also be carried out using any other physiological signal that includes heartbeat information (to the extent that the physiological signal is available on a ventilator), such as for example and without limitation, an electrocardiogram. Furthermore, breath attributes are referred to throughout the present disclosure, particularly with respect to performing the steps of method 100, and it will be appreciated that breath attributes should be read to include PPG data (or the data of any other physiological signal that includes heartbeat information) where method 150 is performed instead of method 100.

Figure 8:
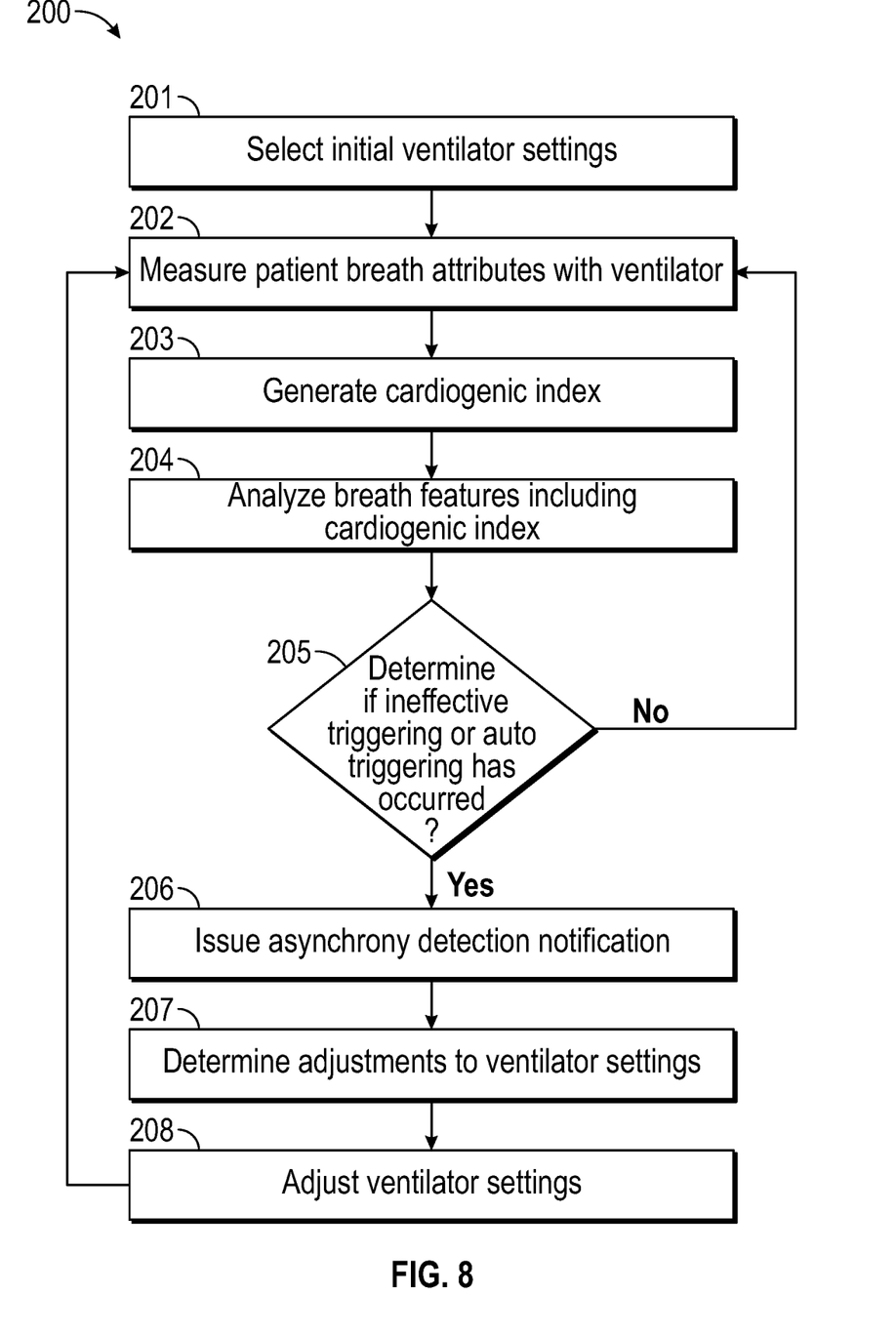
FIG. 8 is a flow chart of a process that uses the either of the methods shown in the flow charts of FIG. 4 and FIG. 6 to dynamically assess and adjust ventilator settings while a ventilator is in use.

The utility of the cardiogenic index lies in how it can be used in an ongoing process of dynamically assessing and adjusting ventilator settings to maximize the efficacy of respiratory treatment for a patient. FIG. 8 is a flow chart of such a process 200 of dynamic assessment and adjustment of ventilator settings. The process 200 is executed by a controller that, in an exemplary embodiment, is included in a ventilator delivering respiratory therapy to a patient. At 201, initial ventilator settings are selected by a caregiver. At 202, patient breath attributes are measured by the ventilator. Examples of breath attributes measured at 202 include but are not limited to airway pressure and airway flow. At 203, the cardiogenic index is calculated using method 100 (or using method 150, if PPG data is available on the ventilator) based on the breath attributes measured at 202. In an exemplary embodiment, the cardiogenic index is continuously calculated while the ventilator is in use by a controller included in the ventilator, and is calculated on a rolling 15-second breath-by-breath basis such that the cardiogenic index at any given moment in time reflects the patient breath feature data of the preceding 15 seconds. It will be appreciated that the cardiogenic index could be calculated on a rolling basis for a period of time less than or greater than 15 seconds without departing from the disclosed concept. As is described in more detail herein with respect to FIG. 10 and as shown at 204 and 205, in an exemplary embodiment, a machine learning model included in the controller analyzes a number of breath features generated from the breath attributes measured at 202, including the cardiogenic index, to determine if ineffective triggering or auto triggering has occurred. If at 204 and 205 the machine learning model determines that a PVA has occurred, the controller issues an asynchrony detection notification at 206. For example and without limitation, the controller could sound a tone, issue a written message on the ventilator screen, or perform a combination thereof to alert a caregiver that a PVA has occurred. It will be appreciated that process 200 returns to 202 if a PVA is not detected.

After an asynchrony detection notification is issued at 206, the process continues on to 207 where the controller may issue preprogrammed recommended adjustments to the ventilator settings or where the caregiver may make his or her own determination about adjustments that need to be made to the ventilator settings. After the adjustments are recommended by the controller or determined by the caregiver at 207, the process proceeds to 208, where the ventilator settings are adjusted in accordance with the adjustments determined at 207. The process then returns to 202. It will be appreciated that method 100 can be executed continuously throughout the duration of use of the ventilator.

Method 100 represents an improvement over existing methods for identifying PVAs that do not use cardiogenic artefacts to identify PVA occurrences. Using cardiogenic artefacts to classify a ventilator-delivered breath or lack thereof as a PVA permits close to real-time notifications of the occurrence of PVAs to be issued by the ventilator, reducing or even eliminating the need for a respiratory therapist, intensivist, or other caregiver to manually determine the occurrence of PVAs on a breath-by-breath basis. Accordingly, more timely adjustments to ventilator settings can be made to prevent the recurrence of PVAs and minimize patient discomfort and other undesirable outcomes that often result from undetected PVAs persisting for prolonged periods of time. In addition, the use of method 100 facilitates more meaningful monitoring of long term trends (on the scale of up to 76 hours) resulting from adjustments made to a patient's respiratory therapy, enabling caregivers to better understand how their adjustments to ventilator settings affect asynchrony trends.

In the non-limiting exemplary embodiment, in order to implement process 200, particularly steps 204-205, a machine learning model is trained to use a cardiogenic index calculated from ventilator waveform data using method 100 so that a controller within the ventilator can be configured to execute the machine learning model. Training machine learning models to use cardiogenic artefacts present in ventilator waveforms in order to detect PVAs represents another improvement over prior art systems and methods for identifying PVAs.

Figure 9:
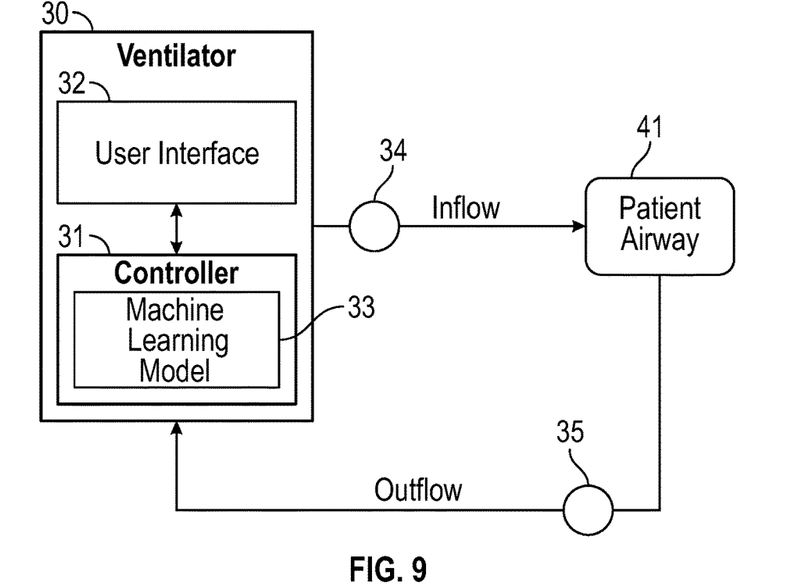
FIG. 9 is a schematic diagram of a ventilator including a machine learning model for detecting PVAs according to an exemplary embodiment of the disclosed concept.

FIG. 9 is a simplified schematic depiction of an exemplary ventilator 30 according to such a non-limiting exemplary embodiment of the disclosed concept. Ventilator 30 includes a controller 31 that accepts input from a user interface 32 and sends output to the user interface 32. In an exemplary embodiment, a machine learning model 33 is software integrated into the controller 31, as shown in FIG. 9. The user interface 32 includes a screen and allows a caregiver to instruct the controller 31 to select the settings of the ventilator 30 via input mechanisms included in the user interface 32, and also displays outputs from the controller 31 such as waveforms of the patient's breathing activity. The airflow generated by ventilator 30 and provided to the patient airway 41 exits the ventilator 30 via the inflow pathway and the air expired through the patient airway 41 is returned to the ventilator via the outflow pathway. The ventilator 30 may include a number of inflow sensors 34 or outflow sensors 35 structured to measure airway pressure, flow, and/or other breath attributes. It will be appreciated that the inflow sensors 34 and outflow sensors 35 are in either direct or indirect communication with controller 31 to enable controller 31 to monitor and analyze the data measured by the sensors 34, 35.

Figure 10:
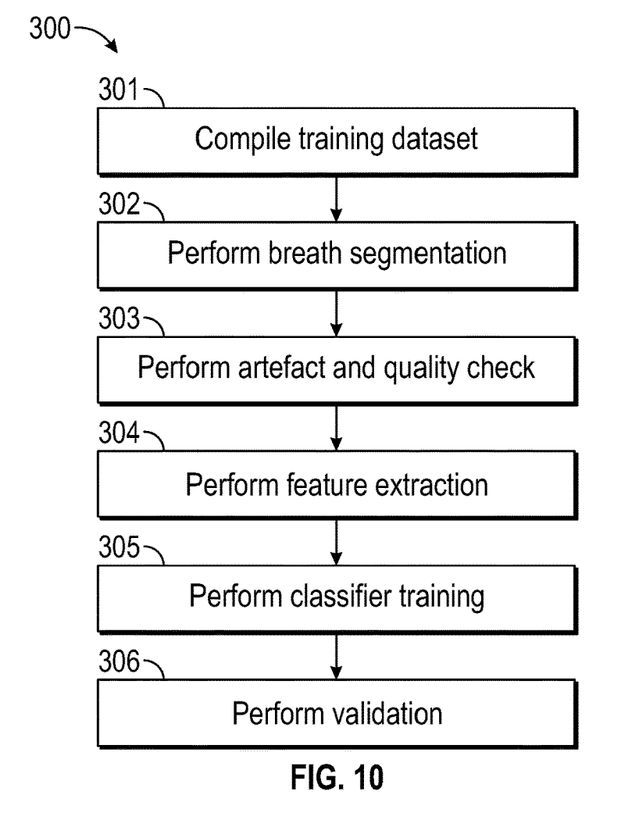
FIG. 10 is a flow chart of a method for training a machine learning model to detect PVAs in ventilator waveforms according to an exemplary embodiment of the disclosed concept.

FIG. 10 is a flow chart of a method 300 used to train a machine learning model such as the model 33 shown in FIG. 9 to detect an ineffective triggering or auto triggering PVA using a cardiogenic index, in accordance with an exemplary embodiment of the disclosed concept. At 301, a training dataset is compiled. In one non-limiting exemplary embodiment, the training dataset is compiled from ventilator waveform data of several patients as well as from laboratory ventilators simulating patient breathing efforts. In another non-limiting exemplary embodiment, the training dataset is compiled solely from patient ventilator waveform data. It will be appreciated that the more patients whose data is used to train the machine learning model, the more accurate the machine learning model may be. Using data from at least 20 patients be may preferable, but there is no requisite minimum number of patients whose data should be collected. It will also be appreciated that data for a different quantity of breaths may be collected from each patient without departing from the scope of the disclosed concept. For example and without limitation, breath data for 100 breaths of one patient may be used while breath data for 45 breaths of another patient may be used.

At 302, breath segmentation is performed on the training dataset patient ventilator waveforms, wherein the patient waveforms are analyzed manually and labeled to denote the start of inhalation and start of exhalation throughout each waveform, as well as to label any observed PVAs (this step may be skipped if ventilator flags, identifying the time a breath was delivered, are available). Breath labelling is preferably performed by an expert. Non-limiting examples of experts include intensivists, respiratory therapists, and anesthesiologists. It may be preferable to label a perceived PVA as a PVA only if two or more experts agree that a PVA occurred. It will be appreciated that breath segmentation does not need to be performed on laboratory-simulated patient ventilator efforts, as the simulating program can provide the breath segmentation information. At 303, an artefact and quality check is performed on the training set patient ventilator waveforms by manually removing mandatory breaths used for estimating lung mechanics or for purging the ventilator sensors (since auto triggering and ineffective triggering PVAs arise in the context of assist mode ventilation), as well any other signals attributable to the ventilator sensors rather than patient breathing.

At 304, feature extraction is performed on the training dataset, wherein several features used for classifying asynchrony events are calculated for each breath by gathering all data from the breath and mapping the data to a small vector of values. Cardiogenic index is one such feature extracted at 304, using method 100 or method 150. Other features that can be extracted at 304 may include, for example, and without limitation, ratio between inhalation and exhalation durations (used to classify auto triggering PVAs), estimated patient inspiratory effort at the start of the inhalation phase (also used to classify auto triggering PVAs), and average airway pressure slope of estimated patient forced effort during exhalation phase (used to classify ineffective triggering PVAs). Several of the features that can be extracted at 303 are unique to the detection of either auto triggering or ineffective triggering, but cardiogenic index is extracted as a feature used in the classification of both auto triggering and ineffective triggering. In laboratory trials, the use of cardiogenic index in addition to other features used to classify auto triggering and ineffective triggering incidents increased the efficacy of the machine learning model as compared to trials where cardiogenic index was not used as a classifying feature.

At 305, classifier training is performed, wherein the machine learning model is provided with the training dataset such that it can analyze the segmented breaths and labeled PVAs along with the extracted features in order to detect patterns indicative of both auto triggering PVAs and ineffective triggering PVAs for the purpose of learning to identify PVAs in raw ventilator waveform data. Cross validation may be performed as a first step, wherein the training set data is divided into a number of groups such that the data from some of the groups is used to train the machine learning model in pattern recognition while the raw ventilator data of the other groups are used to test the pattern recognition capability of the machine learning model and repeating the process a number of times while switching the training and test groups. It may be preferable to only use patient data to train the machine learning model in the early stages of cross validation and then augment the training data with the laboratory ventilator-simulated data in later stages (if simulated data is to be used at all). At 306, validation is performed, wherein test data that has not been used in the training set is provided to the machine learning model to analyze for the occurrence of PVAs, and the machine learning model's performance is evaluated manually.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of adjusting ventilator settings to prevent an occurrence of a patient-ventilator asynchrony (PVA), comprising:
    measuring, by one or more sensors associated with a ventilator operating in assist mode and using first ventilator settings, a number of breath attribute signals of a patient receiving respiration assistance from the ventilator;
    executing, by a controller operatively coupled to the one or more sensors, program code stored in a non-transitory machine readable medium configured to generate a cardiogenic index from the number of breath attribute signals and configured to analyze at least the cardiogenic index to determine whether a PVA has occurred based on the cardiogenic index;
    indicating, using an interface associated with the ventilator, an asynchrony detection after determining that a PVA has occurred;
    issuing, using the controller, one or more preprogrammed recommended adjustments to the first ventilator settings to address the PVA that has occurred; and
    adjusting the ventilator settings in accordance with the one or more preprogramed recommended adjustments;
    wherein the number of breath attribute signals includes one or more of a flow rate waveform and an airway pressure waveform;
    the cardiogenic index being generated by one or more of:
    applying spectral analysis to the one or more of the flow rate waveform and the airway pressure waveform to determine a standardized cardiogenic signal; and
    cross-correlating a photoplethysmogram (PPG) signal with the one or more of the flow rate waveform and the airway pressure waveform to determine a signal to noise ratio indicative of the cardiogenic index.

2. The method of claim 1, wherein to analyze comprises:
    comparing the cardiogenic index to a number of predetermined conditions indicative of PVA occurrence; and
    making a determination that a PVA has occurred if the cardiogenic index meets the number of predetermined conditions indicative of PVA occurrence.

3. The method of claim 1, wherein the number of breath attribute signals is measured in a time domain.

4. A method of adjusting ventilator settings to prevent an occurrence of a patient-ventilator asynchrony (PVA), comprising:
    measuring, by one or more sensors associated with a ventilator operating in assist mode and using first ventilator settings, a number of breath attribute signals of a patient receiving respiration assistance from the ventilator;
    executing, by a controller operatively coupled to the one or more sensors, program code stored in a non-transitory machine readable medium configured to generate a cardiogenic index from the number of breath attribute signals and configured to analyze at least the cardiogenic index to determine whether a PVA has occurred based on the cardiogenic index;
    indicating, using an interface associated with the ventilator, an asynchrony detection after determining that a PVA has occurred;
    issuing, using the controller, one or more preprogrammed recommended adjustments to the first ventilator settings to address the PVA that has occurred; and
    adjusting the ventilator settings in accordance with the one or more preprogramed recommended adjustments;
    wherein to generate the cardiogenic index comprises:
    standardizing the number of breath attribute signals to produce a number of standardized breath signals;
    summing the number of standardized breath signals to produce a cumulative breath signal such that a data value for a given x-axis value from each standardized breath signal is added to corresponding data values from the same given x-axis value from all other standardized breath signals;
    generating a power spectrum of the cumulative breath signal;
    normalizing power distribution values in the power spectrum that fall within a predetermined cardiogenic frequency range; and
    producing a reconstructed cardiogenic signal by transforming the normalized power distribution values from the predetermined frequency range into a time domain signal.

5. The method of claim 4, wherein the number of breath attribute signals includes a pressure waveform signal including pressure waveform data and a flow waveform signal including flow waveform data, and wherein the number of standardized breath signals includes a standardized pressure waveform signal and a standardized flow waveform signal.

6. The method of claim 4, wherein a lower boundary of the cardiogenic frequency range is 1.2 Hz and an upper boundary of the cardiogenic frequency range is 20 Hz.

7. The method of claim 4, wherein normalizing the power distribution values in the power spectrum further comprises:

finding the sum of all of the power distribution values included within a first Nyquist zone; and dividing each power distribution value within the cardiogenic frequency range by the sum of all of the power distribution values within the first Nyquist zone, wherein a lower boundary of the first Nyquist zone is 0 Hz.

8. The method of claim 7, wherein an upper boundary of the first Nyquist zone is the upper boundary of the cardiogenic frequency range.

9. The method of claim 4, wherein to analyze comprises:
comparing the cardiogenic index to a number of predetermined conditions indicative of PVA occurrence; and
making a determination that a PVA has occurred if the cardiogenic index meets the number of predetermined conditions indicative of PVA occurrence.

10. The method of claim 4, wherein the number of breath attribute signals is measured in a time domain.

11. The method of claim 1, wherein the number of breath attribute signals includes a photoplethysmogram (PPG) signal; and
wherein a cardiogenic signal power is estimated from the PPG signal.

12. The method of claim 1, wherein the PVA is one of an auto triggering PVA or an ineffective triggering PVA.

13. The method of claim 1, wherein to determine comprises:
using a machine learning model to make a determination that a PVA has occurred based on the cardiogenic index.

14. The method of claim 4, wherein the number of breath attribute signals includes a photoplethysmogram (PPG) signal; and
wherein a cardiogenic signal power is estimated from the PPG signal.

15. The method of claim 4, wherein the PVA is one of an auto triggering PVA or an ineffective triggering PVA.

16. The method of claim 4, wherein to determine comprises:
using a machine learning model to make a determination that a PVA has occurred based on the cardiogenic index.

17. A ventilator comprising:
a controller;
a non-transitory storage medium storing program code;
an inflow pathway configured to provide air from the ventilator into an airway of a patient;
an outflow pathway configured to receive expired air from the airway of the patient; and
a number of sensors configured to measure data about a number of patient breath attributes of the patient receiving respiration assistance from the ventilator operating in assist mode and using first ventilator settings,
wherein the controller is configured to receive data measured by the number of sensors,
wherein the controller is configured to execute the program code, the program code being configurable to:
generate a cardiogenic index based on the data measured by the number of sensors;
analyze at least the cardiogenic index to determine whether a PVA has occurred;
issue one or more preprogrammed recommended adjustments to the first ventilator settings to address the PVA that has occurred; and
adjust the ventilator settings in accordance with the one or more preprogramed recommended adjustments;

wherein the program code configured to generate the cardiogenic index comprises program code configured for:
standardizing the data about the number of patient breath attributes to produce a number of standardized breath signals;
summing the number of standardized breath signals to produce a cumulative breath signal such that a data value for a given x-axis value from each standardized breath signal is added to corresponding data values from the same given x-axis value from all other standardized breath signals;
generating a power spectrum of the cumulative breath signal;
normalizing power distribution values in the power spectrum that fall within a predetermined cardiogenic frequency range; and
producing a reconstructed cardiogenic signal by transforming the normalized power distribution values from the predetermined frequency range into a time domain signal.

18. A ventilator comprising:
a controller;
a non-transitory storage medium storing program code;
an inflow pathway configured to provide air from the ventilator into an airway of a patient;
an outflow pathway configured to receive expired air from the airway of the patient; and
a number of sensors configured to measure data about a number of patient breath attributes of the patient receiving respiration assistance from the ventilator operating in assist mode and using first ventilator settings,
wherein the controller is configured to receive data measured by the number of sensors,
wherein the controller is configured to execute the program code, the program code being configurable to:
generate a cardiogenic index based on the data measured by the number of sensors;
analyze at least the cardiogenic index to determine whether a PVA has occurred;
issue one or more preprogrammed recommended adjustments to the first ventilator settings to address the PVA that has occurred; and
adjust the ventilator settings in accordance with the one or more preprogramed recommended adjustments;
wherein the data about the number of patient breath attributes include a pressure waveform signal including pressure waveform data and a flow waveform signal including flow waveform data;
the cardiogenic index being generated by one or more of:
applying spectral analysis to the one or more of the flow waveform data and the pressure waveform data to determine a standardized cardiogenic signal; and
cross-correlating a photoplethysmogram (PPG) signal with the one or more of the flow waveform data and the pressure waveform data to determine a signal to noise ratio indicative of the cardiogenic index.

19. The ventilator of claim 18,
wherein the controller comprises a machine learning model,
wherein the machine learning model is trained to recognize conditions indicative of a PVA occurrence, wherein the machine learning model is trained to determine if a PVA has occurred using at least the cardiogenic index, and wherein controller is configured to issue an asynchrony detection notification if the machine learning model determines that a PVA has occurred.

20. The ventilator of claim 18,
wherein the controller comprises a machine learning model,
wherein the machine learning model is trained to recognize conditions indicative of a PVA occurrence, wherein the machine learning model is trained to determine if a PVA has occurred using at least the cardiogenic index, and wherein the machine learning model is trained to identify auto triggering PVAs and ineffective triggering PVAs.

\* \* \* \* \*